(12) United States Patent
Isogai

(10) Patent No.: US 10,022,050 B2
(45) Date of Patent: Jul. 17, 2018

(54) TERMINAL DEVICE, NON-TRANSITORY STORAGE MEDIUM HAVING STORED THEREON TERMINAL CONTROL PROGRAM, AND OPTOMETRY SYSTEM

(71) Applicant: NIDEK CO., LTD., Gamagori-shi, Aichi (JP)

(72) Inventor: Naoki Isogai, Nishio (JP)

(73) Assignee: NIDEK CO., LTD., Gamagori-shi (JP)

( * ) Notice: Subject to any disclaimer, the term of this patent is extended or adjusted under 35 U.S.C. 154(b) by 0 days.

(21) Appl. No.: 15/221,763

(22) Filed: Jul. 28, 2016

(65) Prior Publication Data

US 2017/0027445 A1    Feb. 2, 2017

(30) Foreign Application Priority Data

Jul. 31, 2015   (JP) ................... 2015-152051

(51) Int. Cl.
| | |
|---|---|
| *A61B 3/14* | (2006.01) |
| *A61B 3/18* | (2006.01) |
| *A61B 3/00* | (2006.01) |

(52) U.S. Cl.
CPC .............. *A61B 3/18* (2013.01); *A61B 3/0025* (2013.01); *A61B 3/0033* (2013.01); *A61B 3/0058* (2013.01); *A61B 3/14* (2013.01)

(58) Field of Classification Search
CPC ....... A61B 3/18; A61B 3/0025; A61B 3/0033; A61B 3/0058; A61B 3/14
USPC ......................................... 351/206, 205, 200
See application file for complete search history.

(56) References Cited

U.S. PATENT DOCUMENTS

| | | | | | |
|---|---|---|---|---|---|
| 5,587,748 | A | * | 12/1996 | Luce ................... | A61B 3/0075 351/205 |
| 8,419,184 | B1 | * | 4/2013 | Butler ................. | A61B 3/0285 351/205 |

FOREIGN PATENT DOCUMENTS

| | | |
|---|---|---|
| EP | 3001943 A1 | 4/2016 |
| JP | 2012-213489 A | 11/2012 |
| JP | 2014-202700 A | 10/2014 |
| JP | 2016-067795 A | 5/2016 |

\* cited by examiner

*Primary Examiner* — Tuyen Tra
(74) *Attorney, Agent, or Firm* — Oliff PLC

(57) ABSTRACT

A terminal device to operate a plurality of ophthalmic apparatuses includes a communication unit to perform communication with the ophthalmic apparatuses, a selection receiving unit to receive a selection command to select at least one ophthalmic apparatus as an operation target to be operated from among the ophthalmic apparatuses, and a control unit to transmit a control signal to the operation target ophthalmic apparatus through the communication unit.

19 Claims, 10 Drawing Sheets

TERMINAL DEVICE, NON-TRANSITORY STORAGE MEDIUM HAVING STORED THEREON TERMINAL CONTROL PROGRAM, AND OPTOMETRY SYSTEM

CROSS-REFERENCE TO RELATED APPLICATION

This application claims priority from Japanese Patent Application No. 2015-152051 filed with the Japan Patent Office on Jul. 31, 2015, the entire content of which is hereby incorporated by reference.

BACKGROUND

1. Technical Field

The present disclosure relates to a terminal device to operate an ophthalmic apparatus, a non-transitory storage medium having stored thereon a terminal control program, an ophthalmic apparatus to be operated by the terminal device, and an optometry system.

2. Related Art

As an ophthalmic apparatus for examining an examinee's eye, there has been known an OCT (Optical Coherence Tomography) apparatus configured to obtain a tomographic image by use of for example an OCT which uses low coherent light (see Japanese unexamined patent application publication NO. 2012-213489). As other known ophthalmic apparatuses, there are an eye refractive power measuring apparatus, an intraocular pressure measuring apparatus, a fundus camera, a scanning laser ophthalmoscope (SLO), a reflector, and others.

Heretofore, those ophthalmic apparatus are generally subjected to alignment with respect to an examinee's eye by means of an operation unit provided in each of the apparatuses.

SUMMARY

For the conventional ophthalmic apparatus, an apparatus adapted to full-automatically perform a sequence of operation from alignment to measurement has been proposed. This apparatus enables an examiner to make measurement with only simple operation.

However, when a plurality of apparatuses are to be handled or managed, the examiner has to come and go between the apparatuses in order to operate an operation unit of each apparatus. Even for simple operation, such moving back and forth between the apparatuses is burdensome to the examiner.

One of purposes of the present disclosure is to provide a terminal device configured to easily handle or manage a plurality of ophthalmic apparatuses, a non-transitory storage medium having stored thereon a terminal control program, an ophthalmic apparatus to be operated by the terminal device, and an optometry system.

To achieve the above purpose, one aspect of the present disclosure provides a terminal device to operate a plurality of ophthalmic apparatuses, the terminal device comprising: a communication unit configured to perform communication with the plurality of ophthalmic apparatuses; a selection receiving unit configured to receive a selection command to select at least one ophthalmic apparatus as an operation target to be operated from among the plurality of ophthalmic apparatuses; and a control unit configured to transmit a control signal to the ophthalmic apparatus selected as the operation target through the communication unit.

To achieve the above purpose, another aspect of the present disclosure provides a non-transitory storage medium having stored thereon a terminal control program to be used in a terminal device to operate a plurality of ophthalmic apparatuses, the program being executable by a processor of the terminal device to cause the terminal device to execute the steps of: receiving a selection command to select at least one ophthalmic apparatus which is an operation target to be operated from among the plurality of ophthalmic apparatuses; and transmitting a control signal to the ophthalmic apparatus selected as the operation target.

To achieve the above purpose, still another aspect of the present disclosure provides an optometry system to examine an examinee's eye, comprising: a plurality of ophthalmic apparatuses to examine the examinee's eye; and a terminal device to operate the ophthalmic apparatuses, the terminal device including: a communication unit configured to perform communication with the ophthalmic apparatuses; a selection receiving unit configured to receive a selection command to select at least one ophthalmic apparatus as an operation target to be operated from among the ophthalmic apparatuses; and a control unit configured to transmit a control signal to the ophthalmic apparatus selected as the operation target through the communication unit.

DETAILED DESCRIPTION

Figure 1:
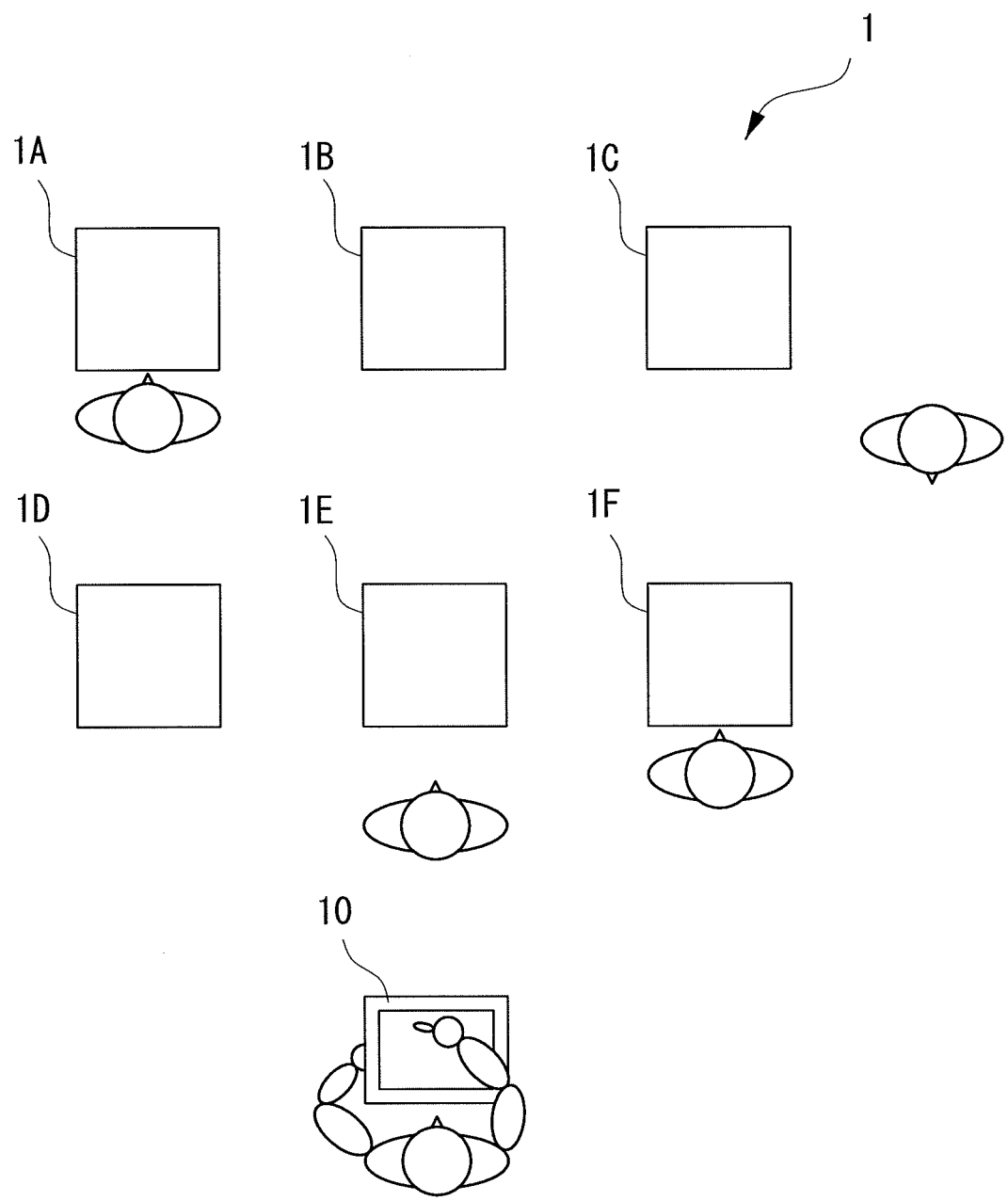
FIG. 1 is a diagram showing a usage example of a terminal device in an example.

An embodiment which is one of typical embodiments of this disclosure will be briefly explained below referring to the accompanying drawings.

A terminal device (e.g., a terminal device 10) in the present embodiment is configured to operate for example a plurality of ophthalmic apparatuses (e.g., ophthalmic apparatuses 1). The terminal device is mainly provided with for example a communication unit (e.g., a communication unit 77 and others), a selection receiving unit (e.g., a display unit 75, an operation unit 76, and others), a control unit (e.g., a control unit 70), and others. The communication unit is configured for example to perform communication with the ophthalmic apparatus or apparatuses. The selection receiving unit is configured for example to receive a selection command to select at least one ophthalmic apparatus as an operation target to be operated (an "operation target ophthalmic apparatus") from among the plurality of ophthalmic apparatuses. The control unit is configured for example to transmit a control signal to the selected operation target ophthalmic apparatus through the communication unit. This enables an examiner to easily operate the plurality of ophthalmic apparatuses by use of the terminal device.

The selection receiving unit may be provided with for example a display unit (e.g., the display unit 75 and others) and an operation receiving unit (e.g., the operation unit 76 and others). The display unit is configured for example to display an operational region used for operating the ophthalmic apparatus or apparatuses. The operational region may be for example an icon, a screen, and others. The operation receiving unit is configured for example to receive an operation from the examiner. In this case, the control unit is configured to cause the display unit to display thereon for example a first operational region (e.g., an icon 21a and others) and a second operational region (e.g., an icon 21b and others). The first operational region is a region displayed on the display unit to operate a first ophthalmic apparatus. The second operational region is a region displayed on the display unit to operate a second ophthalmic apparatus different from the first ophthalmic apparatus. The control unit is further configured to transmit a first control signal for operating the first ophthalmic apparatus to the first ophthalmic apparatus based on the operation received by the operation receiving unit with respect to the first operational region. The control unit is also further configured to transmit a second control signal for operating the second ophthalmic apparatus to the second ophthalmic apparatus based on the operation received by the operation receiving unit with respect to the second operational region. The terminal device in the present embodiment can thus operate a plurality of the ophthalmic apparatuses through the use of a common terminal device.

When three or more ophthalmic apparatuses are to be operated, naturally, three or more operational regions may be displayed on the display unit. For instance, an $n^{th}$ operational region ("n" is a natural number) may be displayed on the display unit, so that an $n^{th}$ control signal for operating an $n^{th}$ ophthalmic apparatus is transmitted to the $n^{th}$ ophthalmic apparatus based on an operation received on the $n^{th}$ operational region by the operation receiving unit.

The control unit may transmit the first control signal and the second control signal to a plurality of ophthalmic apparatuses. In this case, for instance, each control signal may be prefixed with an identifier specifying a target apparatus to which the control signal should be transmitted. Accordingly, a plurality of ophthalmic apparatuses may be each configured to receive a control signal having a corresponding identifier from among signals transmitted from the terminal device. The control unit may also transmit a control signal to a plurality of ophthalmic apparatuses so that only an ophthalmic apparatus(es) that is in an active state receives the control signal(s).

The control unit may obtain a first observed image (e.g., an observed image 24a and others) and a second observed image (e.g., an observed image 24f and others) through the communication unit. The first observed image is for example an image of an examinee's eye photographed by the first ophthalmic apparatus. The second observed image is for example an image of an examinee's eye photographed by the second ophthalmic apparatus. In this case, the control unit displays the first observed image in the first operational region and the second observed image in the second operational region. This allows the examiner to visually check a plurality of the observed images of an examinee's eye measured by the plurality of ophthalmic apparatuses.

The control unit may cause the display unit to selectively display the first operational region and the second operational region. In this case, each operational region can be displayed in a large size on the display unit, which is easy to look. Further, the control unit may also cause the display unit to simultaneously display the first operational region and the second operational region. This enables the examiner to ascertain the status of each of the ophthalmic apparatuses in one glance.

The control unit also may set either one of the first ophthalmic apparatus and the second ophthalmic apparatus as an operation target to be operated based on an operation received or input on the one of the first operational region and the second operational region by use of the operation receiving unit. When three or more ophthalmic apparatuses are to be operated, naturally, the control unit also may set any one of the first ophthalmic apparatus to the $n^{th}$ ophthalmic apparatus as an operation target to be operated based on an operation on one of the first operational region to $n^{th}$ operational region. In this manner, the control unit may set an operation target to some ophthalmic apparatuses among the plurality of ophthalmic apparatuses.

The control unit may also change the operation target based on an operation received on either of the first operational region and the second operational region by the operation receiving unit. For instance, when the first ophthalmic apparatus is set as the operation target, the control unit may change the operation target from the first ophthalmic apparatus to the second ophthalmic apparatus based on an operation received on the second operational region by the operation receiving unit. This enables the examiner to operate a desired ophthalmic apparatus of the plurality of ophthalmic apparatuses.

When the first ophthalmic apparatus is set as the operation target, the control unit may also cause the display unit to display the first operational region more emphatically than the second operational region to the second ophthalmic apparatus which is unset, or not set, as the operation target. For instance, the control unit may also cause the display unit to display the operational region corresponding to the operation target ophthalmic apparatus by highlight display, dark display, shaded display, and others. The control unit further may also cause the operational region corresponding to the operation target ophthalmic apparatus to be displayed more brightly than other operational regions or displayed partially in different color.

When the first ophthalmic apparatus is set as the operation target, the control unit may also cause the display unit to display the first operational region in a larger size than the second operational region used to operate the second ophthalmic apparatus which is unset as the operation target. This enables the examiner to easily look the status of the ophthalmic apparatus which is performing measurement.

The control unit may also set the order of operating or activating the plurality of ophthalmic apparatuses for measurement ("measurement order") based on an operation received by use of the operation receiving unit. In this case, the control unit may emphatically display the operational regions in turn according to the measurement order. Thus, the examiner can easily ascertain which apparatus has to be next monitored or operated.

Moreover, the control unit may identify whether each of the plurality of ophthalmic apparatuses is in an active state or an inactive state based on a status signal transmitted from the ophthalmic apparatuses through the communication unit.

The control unit may transmit a control signal to the plurality of ophthalmic apparatuses through the communication unit to thereby switch each ophthalmic apparatus between the active state and the inactive state. For instance, the control unit may switch the ophthalmic apparatuses one by one between the active state and the inactive state or may switch the ophthalmic apparatuses together in one operation between the active state and the inactive state.

The control unit may set the measurement order of the plurality of ophthalmic apparatuses based on an operation received by use of the operation receiving unit. For instance, the control unit may set the measurement order based on the order in which the operational regions each corresponding to the ophthalmic apparatuses were operated. For instance, when the control unit performs measurement by using the first ophthalmic apparatus and then the second ophthalmic apparatus according to the measurement order, the control unit may turns the first ophthalmic apparatus to the inactive state and the second ophthalmic apparatus to the active state at the time when the measurement using the first ophthalmic apparatus is terminated.

The control unit may display a mark symbolizing the first ophthalmic apparatus on the first operational region. For example, name, nickname, graphics, etc. may be displayed on the first operational region. Thus, the examiner can easily ascertain to which one of the plurality of ophthalmic apparatuses the operational region corresponds.

Further, the terminal device may also include a voice input unit. In this case, the control unit may transmit a voice input received from the voice input unit to a voice output unit provided in an operation target ophthalmic apparatus through the communication unit. Thus, the examiner can offer an examinee an explanation of an examination.

The terminal device may further include a photographing unit. In this case, the control unit may transmit an image received from the photographing unit to an individual display unit (e.g., a display unit 7a and others) provided in the operation target ophthalmic apparatus through the communication unit. Thus, the examiner can explain with a gesture to an examinee about an examination.

The control unit may execute a terminal control program stored in a storage unit (e.g., a flash memory 72, a storage unit 74, and others). The terminal control program may include for example a selection receiving step and a transmitting step. The selection receiving step is for example a step of receiving a selection command to select at least one ophthalmic apparatus as an operation target to be operated from among the plurality of ophthalmic apparatuses. The transmitting step is for example a step of transmitting a control signal to the operation target ophthalmic apparatus. The terminal control program which can be read and executed by the control unit is stored in a non-transitory storage medium, such as the flash memory 72 and the storage unit 74.

The terminal control program may include a display step, an operation receiving step, a first transmitting step, and a second transmitting step. The display step is for example a step of displaying, on the display unit, each of the first operational region for operating the first ophthalmic apparatus and the second operational region for operating the second ophthalmic apparatus different from the first ophthalmic apparatus. The operation receiving step is for example a step of receiving an operation on the first operational region or the second operational region. The first transmitting step is for example a step of transmitting a first control signal for operating the first ophthalmic apparatus to the first ophthalmic apparatus, based on an operation received on the first operational region in the operation receiving step. The second transmitting step is for example a step of receiving a second control signal for operating the second ophthalmic apparatus to the second ophthalmic apparatus, based on an operation received on the second operational region in the operation receiving step.

Each ophthalmic apparatus to be operated by the terminal device may be provided with for example a notifying unit (e.g., an indicator lamp 8, the voice output unit 9a, the display unit 7a, and others). The notifying unit may notify an examiner or an examinee for example that the relevant ophthalmic apparatus is a target apparatus to be operated by the terminal device.

The control unit may cause the display unit to display a confirmation screen (e.g., an icon screen 20 and others) for checking the statuses of the plurality of ophthalmic apparatuses. Accordingly, the examiner can check the statuses of the ophthalmic apparatuses on the confirmation screen in one glance and thus promptly address abnormality and other defects of the apparatus.

A plurality of terminal devices may be used to operate a plurality of ophthalmic apparatuses. For instance, two or more terminal devices may be associated with the same ophthalmic apparatus. In this case, it may be arranged such that a terminal device given a first authority of operation is enabled to operate the ophthalmic apparatus and a terminal device or devices given a second or later authority of operation is not permitted to operate until after the operation by the first terminal device having the first authority of operation.

The ophthalmic apparatus to be operated by the terminal device may be an objective optometry apparatus or a subjective optometry apparatus.

Examples

The terminal device in a present example will be described below. The terminal device 10 in this example operates for example a plurality of ophthalmic apparatuses 1 (1A to 1F) (see FIG. 1). For instance, the terminal device 10 is connected to the ophthalmic apparatuses 1 so as to perform communication therewith. For instance, the terminal device 10 is connected to the ophthalmic apparatuses 1 by at least one of wire or wireless. For instance, the terminal device 10 may transmit a command signal and others to the ophthalmic apparatus(s) 1 and receive a measurement result(s) and others from the ophthalmic apparatus(s) 1. The terminal device 10 may be for example a tablet PC, a notebook PC, a smartphone, a desktop PC, etc.

The terminal device 10 is provided with for example the control unit 70, the communication unit 77, the operation unit 76, the display unit 75, and others. The control unit 70 is realized for example by a general CPU (Central Processing Unit) 71, the flash memory 72, a RAM 73, and others. The flash memory 72 stores thereon various programs for controlling operations of the terminal device 10, default values, and others. The RAM 73 temporarily stores various types of information. The control unit 70 may consist of a plurality of controllers (that is, a plurality of processors).

Figure 2:
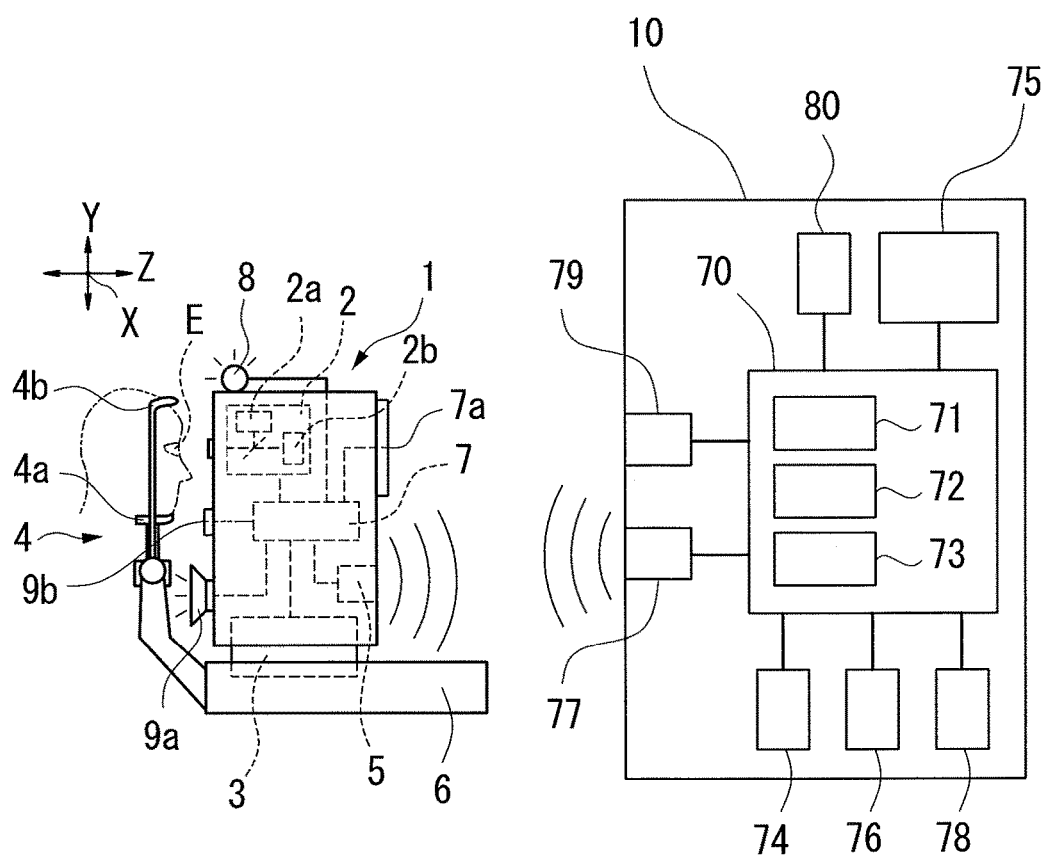
FIG. 2 is a schematic appearance diagram of the terminal device in the example.

The control unit 70 is electrically connected, as shown in FIG. 2, to for example the storage unit 74, the operation unit 76, the display unit 75, the communication unit 77, and others. The storage unit 74 is a non-transitory storage medium that can retain stored contents even when power supply is interrupted. For example, a hard disc drive, a flash ROM, a detachable USB memory, and others may be used as the storage unit 74.

The communication unit 77 performs communication with for example the plurality of ophthalmic apparatuses 1. For instance, the communication unit 77 may transmit and receive radio waves to and from each of the ophthalmic apparatuses 1. The communication unit 77 may perform communication with the ophthalmic apparatuses 1 by for example wireless LAN, infrared communication, WiFi (registered trademark), Bluetooth (registered trademark), etc. This transmission may also utilize an internet connection. As a matter of course, the communication unit 77 may perform communication with each ophthalmic apparatus 1 by wire connection, such as a USB cable and a LAN cable.

The display unit 75 displays for example an operation screen corresponding to each ophthalmic apparatus 1 and a measurement result transmitted from each corresponding ophthalmic apparatus 1. This displaying may use a display of a personal computer (hereinafter, referred to as a "PC"). A plurality of displays may be used in combination. Moreover, the display unit 75 may be provided with a touch panel function.

The operation unit 76 receives various operation commands input by the examiner. The operation unit 76 outputs an operation signal corresponding to the input operation command to the control unit 70. As the operation unit 76, there may be used a user interface, such as at least one of a touch panel, a mouse, a joystick, and keyboard. In the case that the display unit 75 is a touch panel, the display unit 75 also functions as the operation unit 76.

Figure 3:
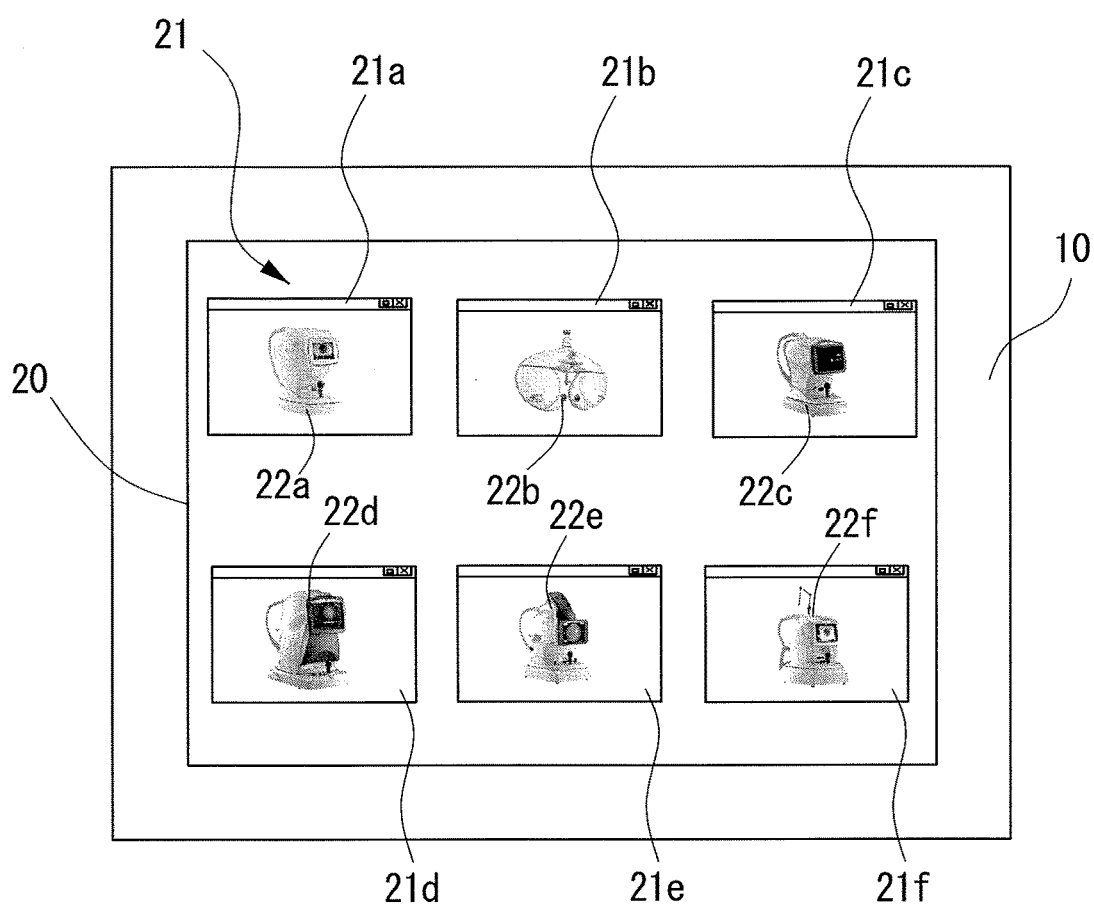
FIG. 3 is a diagram showing one example of an icon screen displayed on the terminal device in the example.

As shown in FIG. 3, for instance, the display unit 75 makes the icon screen 20 appear. The icon screen 20 is a screen for checking the status of and performing the operation of each ophthalmic apparatus 1. On the icon screen 20, icons 21 (21a to 21O corresponding to the ophthalmic apparatuses 1 (1A to 1F) are displayed. Each icon 21 may be for example a screen itself displayed on the display unit 7a of the ophthalmic apparatus or may include an image, a shape, a name, a nickname, and others symbolizing a relevant ophthalmic apparatus 1, or any combination of them. The icons in the present example take the shape of an operation screen displaying an external view 22a to 22f of each apparatus (see FIG. 3). For example, each icon 21a to 21f may have a common shape or different shapes from each other.

On the icon screen 20, two or more icons 21 corresponding to the ophthalmic apparatuses 1 are displayed. For instance, the control unit 70 causes the display unit 75 to display side by side icons corresponding to different ophthalmic apparatuses 1. The examiner checks the status of each ophthalmic apparatus 1, measurement results, and others from each corresponding icon 21 displayed on the display unit 75. Further, the examiner may operate each ophthalmic apparatus 1 by inputting a specific operation on each corresponding icon 21 displayed on the display unit 75.

<About Ophthalmic Apparatus>

The ophthalmic apparatuses 1 connected to the terminal device 10 may include for example an eye refractive power measuring apparatus, a non-contact intraocular tonometer, an axial length measuring apparatus, a corneal endothelial cell photographing apparatus, an optical tomographic image photographing apparatus, a fundus photographing apparatus, a local perimeter, a corneal shape measuring apparatus, a reflector, and others. Each ophthalmic apparatus 1 in the present example is provided with an optometry unit 2 and a drive unit 3 and is configured to measure an examinee's eye in a fully automatic manner. Accordingly, the examiner does not need to operate each apparatus beside the relevant apparatus and can check the status of each ophthalmic apparatus 1 and a measurement result(s) from a place distant from each ophthalmic apparatus 1 by use of the terminal device 10.

For instance, as shown in FIG. 2, the ophthalmic apparatus 1 may be provided with the optometry unit 2, a control unit 7, a communication unit 5, a base table 6, a face support unit 4, a drive unit 3, and others. The control unit 7 is connected to the optometry unit 2, the communication unit 5, the drive unit 3, and others to control the ophthalmic apparatus 1. The communication unit 5 is configured to perform communication with the terminal device 10. For instance, the communication unit 5 transmits and receives radio waves to and from the communication unit 77 of the terminal device 10. The optometry unit 2 is configured to perform examination (measurement, photographing, and others) of an eye of an examinee. The optometry unit 2 is provided with for example an observation optical system 2a, an examination optical system 2b, and others. The observation optical system 2a and the examination optical system 2b each include for example a light source, an optical element (e.g., a lens, a mirror, etc.), a light receiving element (e.g., a CCD, etc.), and others. The drive unit 3 is placed for example on the base table 6 and configured to move the optometry unit 2 in three dimensional directions with respect to the examinee's eye E. The face support unit 4 is configured to support the face or head of the examinee. This face support unit 4 may include for example a chin rest 4a, a forehead rest 4b, and others.

Furthermore, the ophthalmic apparatus 1 may be provided with the display unit 7a, a voice output unit (e.g., a speaker) 9a, a voice input unit (e.g., a microphone) 9b, the indicator lamp (e.g., a pilot lamp) 8, and others. The display unit 7a, the voice output unit 9a, the voice input unit 9b, and the indicator lamp 8 are connected for example to the control unit 7. The display unit 7a is configured to display for example an operation screen, an examination result, and others. The display unit 7a may be provided for example on a side which will face the examinee or on an opposite side to the examinee. The display unit 7a may be configured to change the orientation of a screen so as to face the examinee. The voice output unit 9a may output a predetermined voice guidance stored in an unillustrated storage unit connected to the control unit 7 or may output a voice input by the voice input unit 79 of the terminal device 10. The voice input unit 9b for example inputs the voice of the examinee. With the voice output unit 9a and the voice input unit 9b provided in the ophthalmic apparatus 1 and the voice output unit 79 and the voice input unit 78 provided in the terminal device 10, the examiner can talk with or give an instruction or the like to the examinee even when they are in separated places.

The indicator lamp 8 may be placed for example on the chin rest 4a, the forehead rest 4b, or an upper part of the main unit. The indicator lamp 8 is turned on for example when the apparatus 1 becomes active. By seeing the indicator lamp 8, for instance, the examinee can ascertain whether the apparatus 1 is in an active state (e.g., a measurement enabled state, a power ON state) or in an inactive state (e.g., a sleep state, a power save mode, a power OFF state). The control unit 7 may turn on or blink the indicator lamp 8 of an apparatus to be used for next measurement. This allows the examinee to move to the next ophthalmic apparatus 1 without hesitation. The display unit 7a may also be used as the indicator lamp 8.

<Control Operation>

Figure 4:
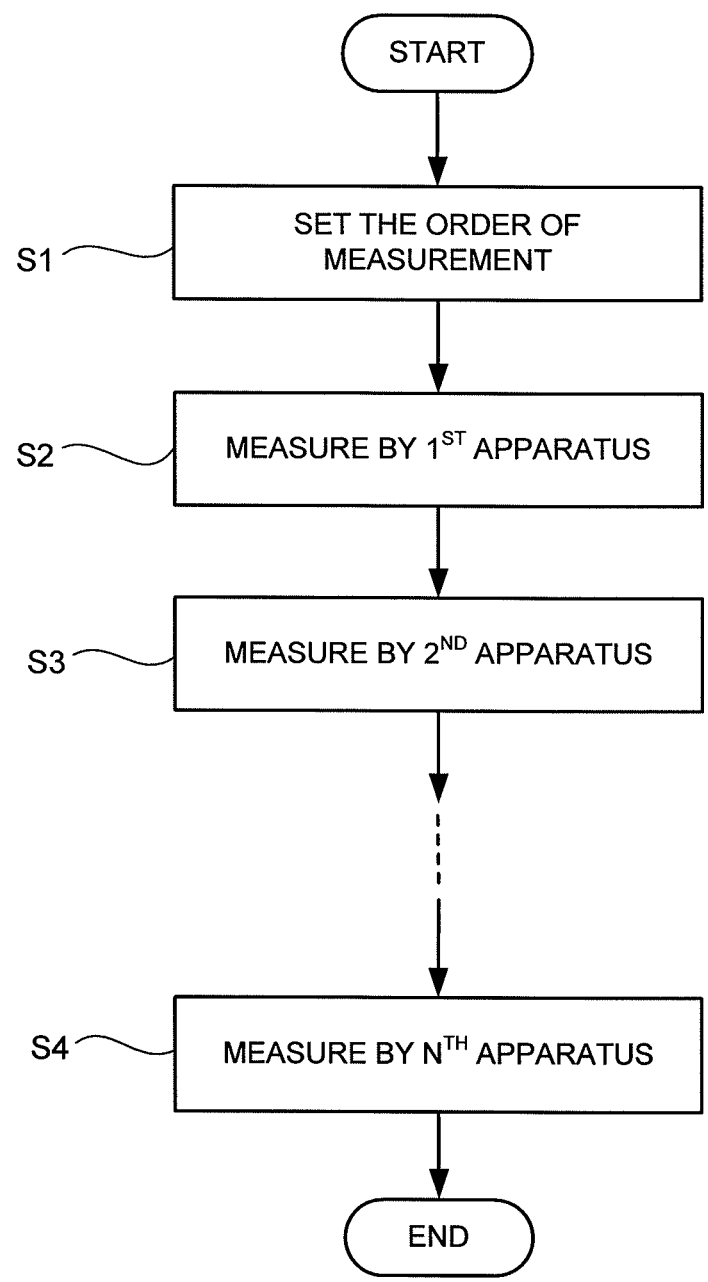
FIG. 4 is a flowchart showing a control action of the terminal device in the example.

Control operations to manage the plurality of ophthalmic apparatuses 1 by use of the terminal device 10 configured as above will be described below referring to flowcharts in FIGS. 4 and 5. For instance, an examiner checks the status of each ophthalmic apparatus 1 and assists measurement by use of the terminal device 10.

The examiner may make settings (e.g., pairing) to associate the terminal device 10 and the ophthalmic apparatuses 1 in advance of measurement. For instance, the control unit 70 may detect radio waves output from each of the ophthalmic apparatuses and store that information (e.g., an identification signal) in the storage unit 74. Thus, the control unit 70 can identify the radio waves from each ophthalmic apparatus.

(Step S1)

Figure 6:
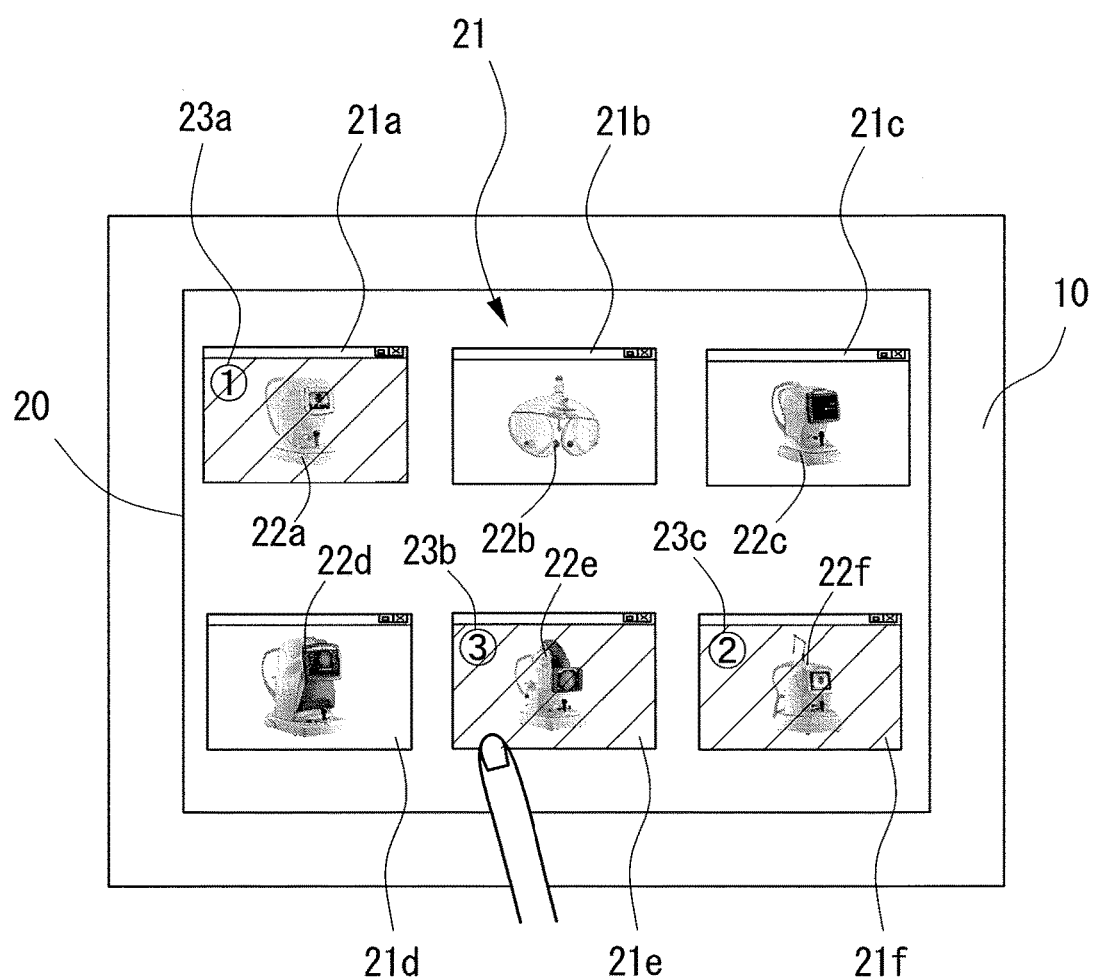
FIG. 6 is a diagram showing one example of a method for setting an order of measurement.

The examiner first sets the measurement order of the plurality of ophthalmic apparatuses 1A to 1F. For instance, as shown in FIG. 6, the examiner may touch the icons 21*a* to 21*f* in the desired order of measurement to thereby input the measurement order to the terminal device 10. When the icon(s) 21 is touched, the display unit 75 detects the touching operation and transmits an operation signal to the control unit 70. The control unit 70 receives for example the operation signal from the display unit 75.

Figure 7:
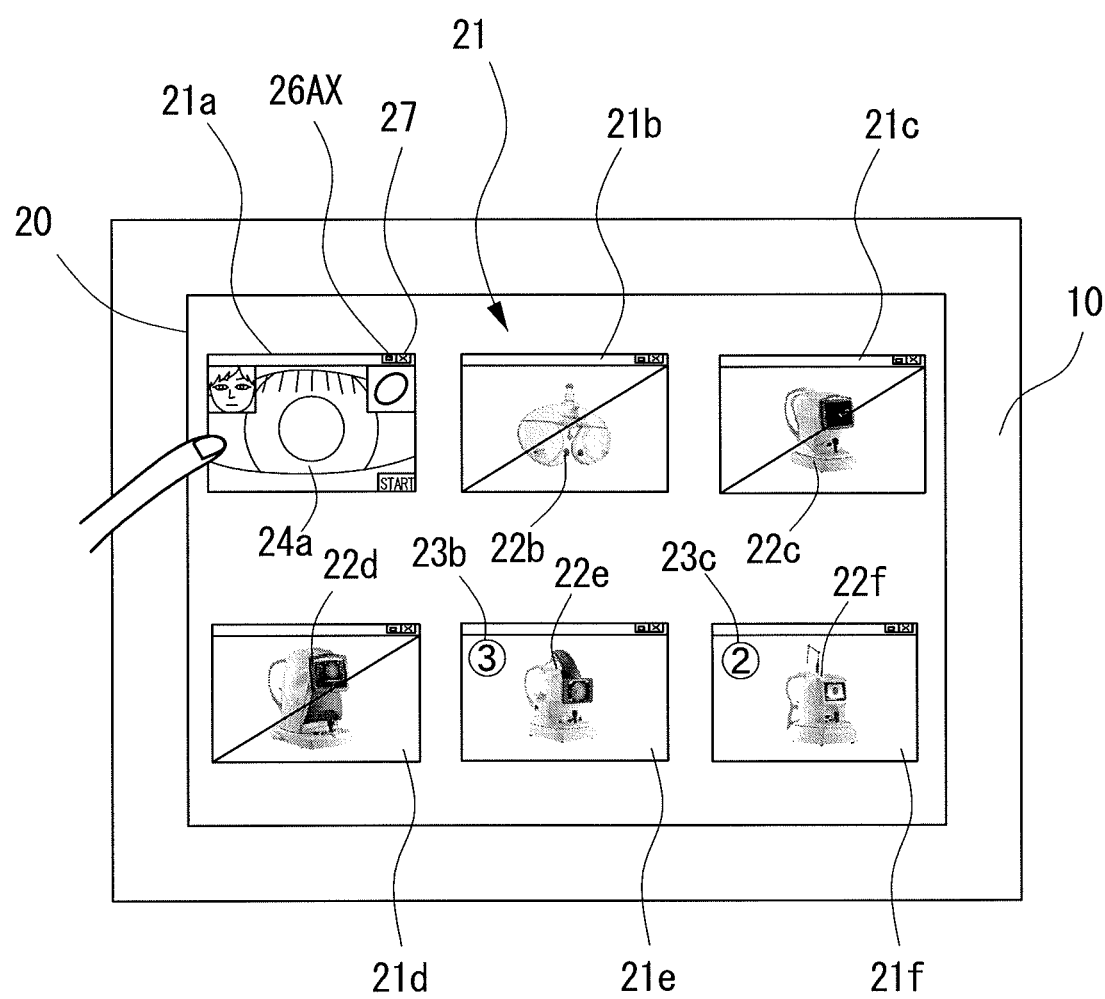
FIG. 7 is a diagram showing one example of an icon screen displayed on the terminal device in the example.

The control unit 70 receives the operation signal output from the display unit 75 and stores the order in which the icons 21 were touched in the storage unit 74. The control unit 70 may change a pictorial display of the icon(s) 21 touched by the examiner and thereby indicate that this icon has been selected. For instance, the control unit 70 may cause the selected icon 21 to be displayed by highlight display, dark display, shaded display, or the like (e.g., see FIGS. 6 and 7). The control unit 70 may display the numbers 23*a* to 23*b* indicating the order of measurement near the selected icon(s) 21. The examiner does not need to select all the ophthalmic apparatuses 1 and has only to select only an apparatus(es) to be used for measurement.

(Step S2)

Figure 5:
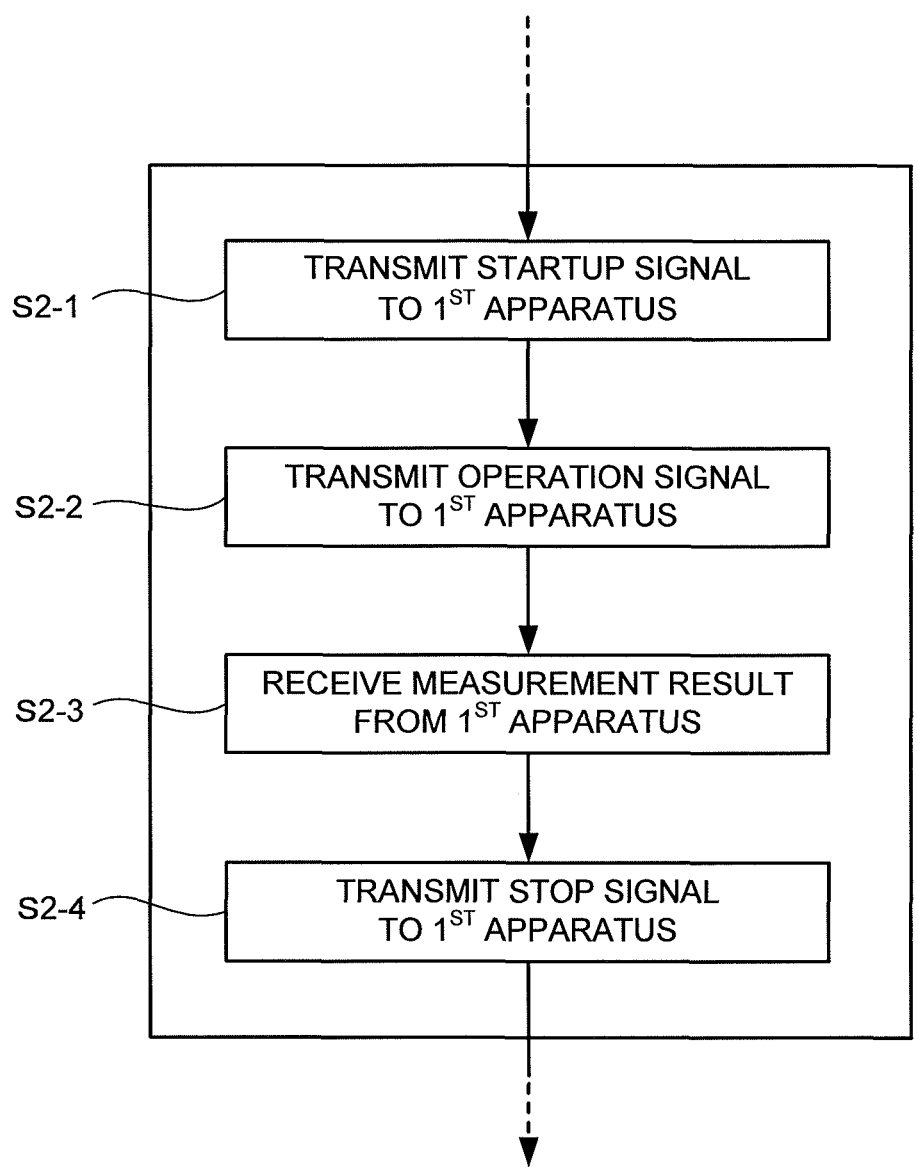
FIG. 5 is a part of the flowchart showing the control action of the terminal device in the example.

The control unit 70 retrieves the measurement order set in step S1 from the storage unit 74 and starts control of the apparatus to be first operated for measurement (e.g., the apparatus 1A) (see FIG. 5). For instance, the control unit 70 transmits a startup signal to the first apparatus 1A through the communication unit 77 (Step S2-1).

When receives the startup signal from the terminal device 10, the control unit 7 of the first apparatus 1A turns the first apparatus 1A to the active state. The control unit 7 of the first apparatus 1A then transmits an observed image 24 photographed by the optometry unit 2 to the terminal device 10. This terminal device 10 receives the observed image 24*a* from the first apparatus 1A and displays this observed image 24*a* on the display unit 75 (see FIG. 7). For instance, the observed image 24*a* may be displayed in a part of the region corresponding to the icon 21*a* in the first apparatus 1A. The icon 21 may also display thereon, in addition to the observed image 24*a*, necessary information, such as a state of the examinee (e.g., a contact state between the face support unit 4 and the examinee's face), a status of the apparatus, and others.

For instance, the examiner may see the observed image displayed in the icon of the first apparatus 1A to ascertain that the first apparatus 1A is in the active state. For instance, the examiner observes the observed image and monitors the way that automatic measurement is being performed. The ophthalmic apparatus 1 automatically makes alignment and measurement.

The terminal device 10 may transmit an operation signal to the ophthalmic apparatus 1 in the active state (Step S2-2). For instance, the examiner may also perform an operation input on the icon 21 to thereby operate the ophthalmic apparatus 1 in the active state. For instance, the examiner may touch the observation image 24*a* displayed in the icon 21*a* and further makes a drag operation, a pinch operation, and others to move the apparatus in X, Y, and Z directions. For instance, the control unit 70 may move the optometry unit 2 of each ophthalmic apparatus 1 in the X and Y directions according to the drag operation by the examiner detected by the display unit 75 (a touch panel) and move the optometry unit 2 of each ophthalmic apparatus 1 in the Z direction according to the pinch operation (see Japanese patent application No. 2014-202700, published as JP-A-2016-67795).

Upon completion of measurement of the examinee's eye E by the first apparatus 1A, the control unit 70 receives measurement results (Step S2-3). For instance, the control unit 70 may transmit a signal to demand status information at regular time intervals to the ophthalmic apparatus 1. Every time receiving the demand signal from the control unit 70, the ophthalmic apparatus 1 may transmit the status information of the apparatus to the terminal device 10. When receives the status information representing the completion of measurement from the ophthalmic apparatus 1, the control unit 70 may request the ophthalmic apparatus 1 to transmit a measurement result. For instance, the ophthalmic apparatus 1 transmits the measurement result to the terminal device 10 in response to a request for the measurement result. It should be understood that the status information, the measurement result, and others may be transmitted unilaterally from the ophthalmic apparatus 1 to the terminal device 10 even if no request is output from the terminal device 10.

The control unit 70 may store the measurement result in the storage unit 74 upon receipt of the measurement result. Further, the control unit 70 may display the measurement result stored in the storage unit 74 in a part of the region corresponding to the relevant icon 21.

Figure 8:
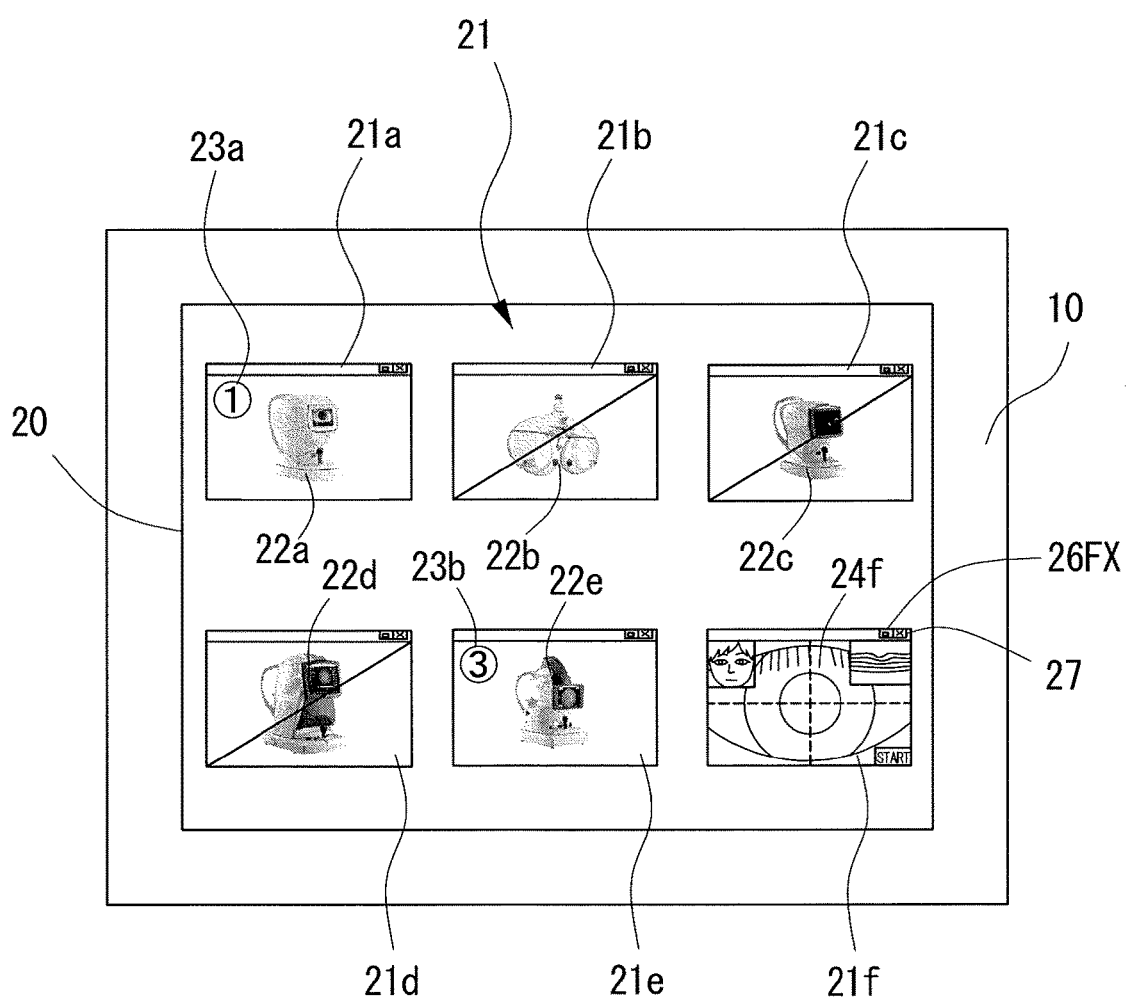
FIG. 8 is a diagram showing one example of an icon screen displayed on the terminal device in the example.

When receives the measurement result from the first apparatus 1A, the control unit 70 may transmit a stop signal to the first apparatus 1A (Step S2-4). In response to the stop signal, the first apparatus 1A turns to the inactive state. Each of the ophthalmic apparatuses 1 is controlled to automatically turn to the inactive state based on the stop signal from the terminal device 10. Thus, unnecessary consumption of electric power is eliminated (see FIG. 8).

(Step S3)

After transmitting the stop signal to the first apparatus 1A, the control unit 70 then transmits a startup signal to the second apparatus 1B. The second apparatus 1B, as with the first apparatus 1A, measures the examinee's eye in response to a measurement start signal from the control unit 70 and transmits a measurement result to the terminal device 10. Upon obtaining the measurement result from the second ophthalmic apparatus 1B, the terminal device 10 turns the second apparatus 1B to the inactive state.

(Step S4)

The control unit 70 repeats the above-described control to perform the measurement in the order set in step S1 and obtains measurement results obtained by the plurality of ophthalmic apparatuses 1A to 1F. The examiner may also output an instruction to the examinee from the voice input unit 79 of the terminal device 10 as needed. Upon completion of measurement by all the ophthalmic apparatuses 1 selected in step S1, for instance, the control unit 70 turns all those ophthalmic apparatuses 1 to the inactive state. The control unit 70 may also cause the display unit 75 to display thereon, in list form, the measurement results obtained by each of the apparatuses.

In the above manner, since the icons 21 individually corresponding to the ophthalmic apparatuses 1 are displayed on the display unit 75, a single terminal device 10 can manage and operate two or more ophthalmic apparatuses 1. Further, since the plurality of ophthalmic apparatuses 1 can be operated by the single terminal device 10, the examiner can operate each apparatus 1 even from a distant or separated place without the need to be near each apparatus 1. Further, the examiner can operate each apparatus 1 from the same place without the need to move to each apparatus.

Moreover, checking the measurement results and operating each apparatus are performed by use of the terminal device 10, so that each apparatus does not have to be provided with either or both of the display unit and the operation unit.

It is of course that a plurality of terminal devices 10 may be provided to control a plurality of ophthalmic apparatuses 1. In this case, only the terminal device 10 given a first authority of operation may be permitted to operate the ophthalmic apparatus(es). At that time, it may be arranged such that other terminal devices 10 having no operation authority are put in a waiting state, and an operating state of the terminal device having the operation authority is displayed on the display unit 75.

In a case of using the plurality of terminal devices 10, the ophthalmic apparatuses may be separated into a plurality of groups and the terminal devices may be allocated one to each group.

In the aforementioned example, the measurement order is set and the active state and the inactive state are switched automatically according to the set measurement order. As an alternative, this switching may be performed according to an operation on the icons 21 by the examiner. For instance, the switching of each apparatus 1 between the active state and the inactive state may be performed by the touch of the icons 21. For instance, when the icon 21 in the inactive state is touched, the control unit 70 may transmit a startup signal to switch the target ophthalmic apparatus 1 to the active state. In contrast, when the stop button 27 in the icon 21 in the active state is touched, the control unit 70 may transmit a stop signal to switch the target ophthalmic apparatus 1 to the inactive state (see FIGS. 7 and 8). The control unit 70 may also change the icon 21 displayed on the display unit 75 to an inactive display.

The control unit 70 may also switch each of the apparatuses separately or switch two or more apparatuses simultaneously. For instance, the control unit 70 may switch the state of all the apparatuses by a specific operation (e.g., long pressing of the relevant icon 21, long pressing of the stop button 27, etc.) by the examiner.

The control unit 70 may also cause the display unit 75 to display the icons 21 by zoom-in display. For instance, when a zoom-in button 26AX provided in the icon 21a (see FIG. 7) is pressed, the control unit 70 may cause the display unit 75 to display an enlarged icon 21AX created by enlarging the icon 21a. This enlarged icon may be similar to an operation screen displayed on the display unit 7a of the ophthalmic apparatus 1.

When the icon 21a is operated, the control unit 70 may cause the display unit 75 to display the enlarged icon 21AX. For instance, when the examiner touches the icon 21a, the control unit 70 may receive an operation signal output from the touch panel and display the enlarged icon 21AX on the display unit 75. For instance, the enlarged icon 21AX displayed on the display unit 75 as shown in FIGS. 9A and 9B enables easy checking of the observed image, operating of the apparatus, and others.

Figure 9A:
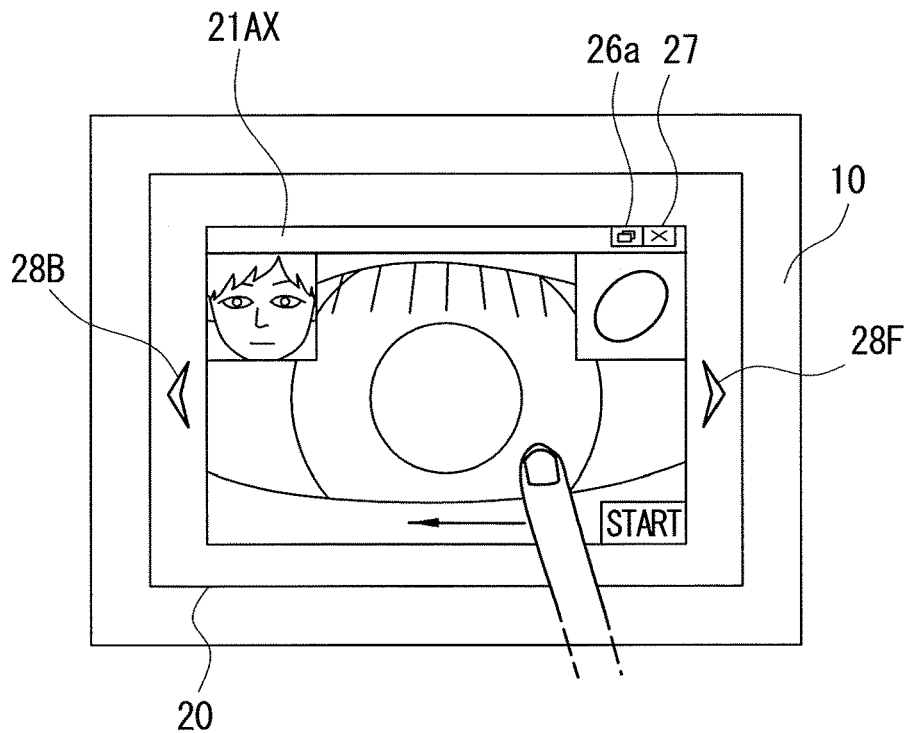
FIGS. 9A and 9B are diagrams showing one example of a zoom-in operation screen displayed on the terminal device in the example.
Figure 9B:
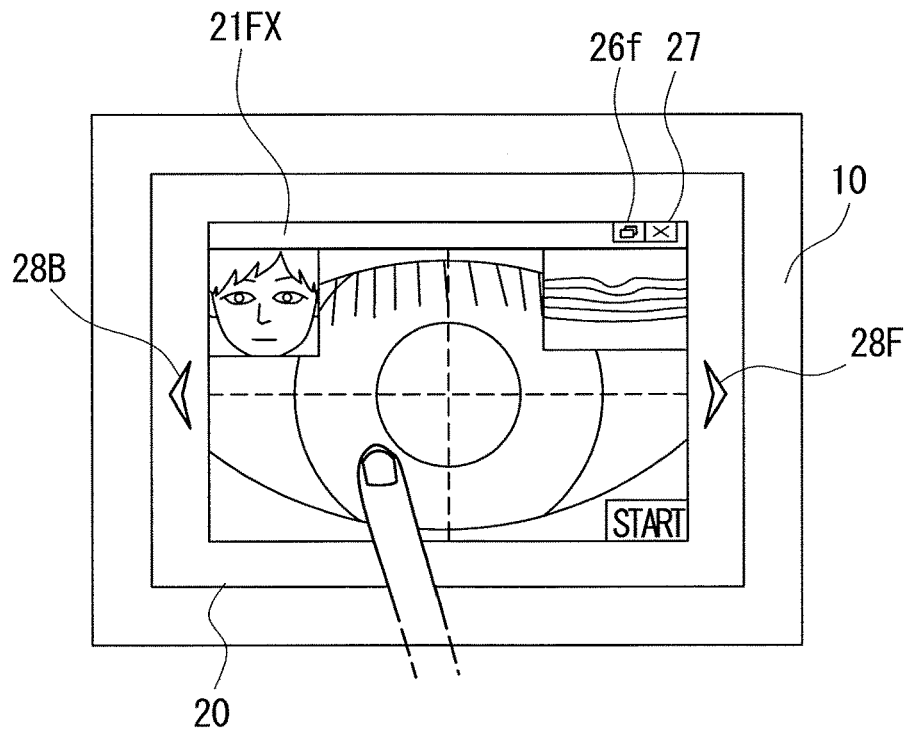

For instance, as shown in FIGS. 9A and 9B, in a case where the enlarged icon 21AX is displayed, an enlarged icon 21FX corresponding to the next measurement order may become displayed by a specific operation, such as a flick operation or a drag operation, on the enlarged icon 21AX. It is of course that the control unit 70 may display a previous or next icon 21 in the measurement order when an icon change-over button 28F or 28B or the like is operated.

When the enlarged icon 21AX is displayed, for instance, upon completion of measurement by the first apparatus 1A, the control unit 70 may automatically change the display to the next enlarged icon 21FX in the measurement order set in step S1.

The enlarged icons 21AX and 21FX may be returned to an original icon size when respective zoom-out buttons 26a and 26f are operated. As a matter of course, the control unit 70 may return the display of the enlarged icon 21AX (21FX) to the original icon 21a (210 upon operation of the stop button 27 of the enlarged icon 21AX (21FX) and simultaneously turn the first apparatus 1A (the second apparatus 1F) to the inactive state.

In the above description, the display unit 75 is provided with a touch panel function and the control unit 70 is configured to detect the touch input by the examiner. However, the present disclosure is not limited thereto. For instance, the terminal device 10 may detect selection of the icon 21 based on an operation by another operation unit. For example, an operation unit, such as a mouse and a keyboard, may be used.

The terminal device 10 may update various settings or software in each ophthalmic apparatus 1. For instance, the control unit 70 may download configuration information, update software, and others of each ophthalmic apparatus 1 through an internet connection and transmit them to each corresponding ophthalmic apparatus 1. The ophthalmic apparatuses 1 may update various settings, software, and others by an update program received from the terminal device 10.

The terminal device 10 may perform communication with the ophthalmic apparatuses 1 through an internet connection. For instance, in case radio waves do not reach between the terminal device 10 and the ophthalmic apparatus(s) 1, signals may be transmitted and received therebetween through the internet connection. In this manner, the examiner may remotely operate the ophthalmic apparatus(s) 1 through the use of the internet connection.

Figure 10:
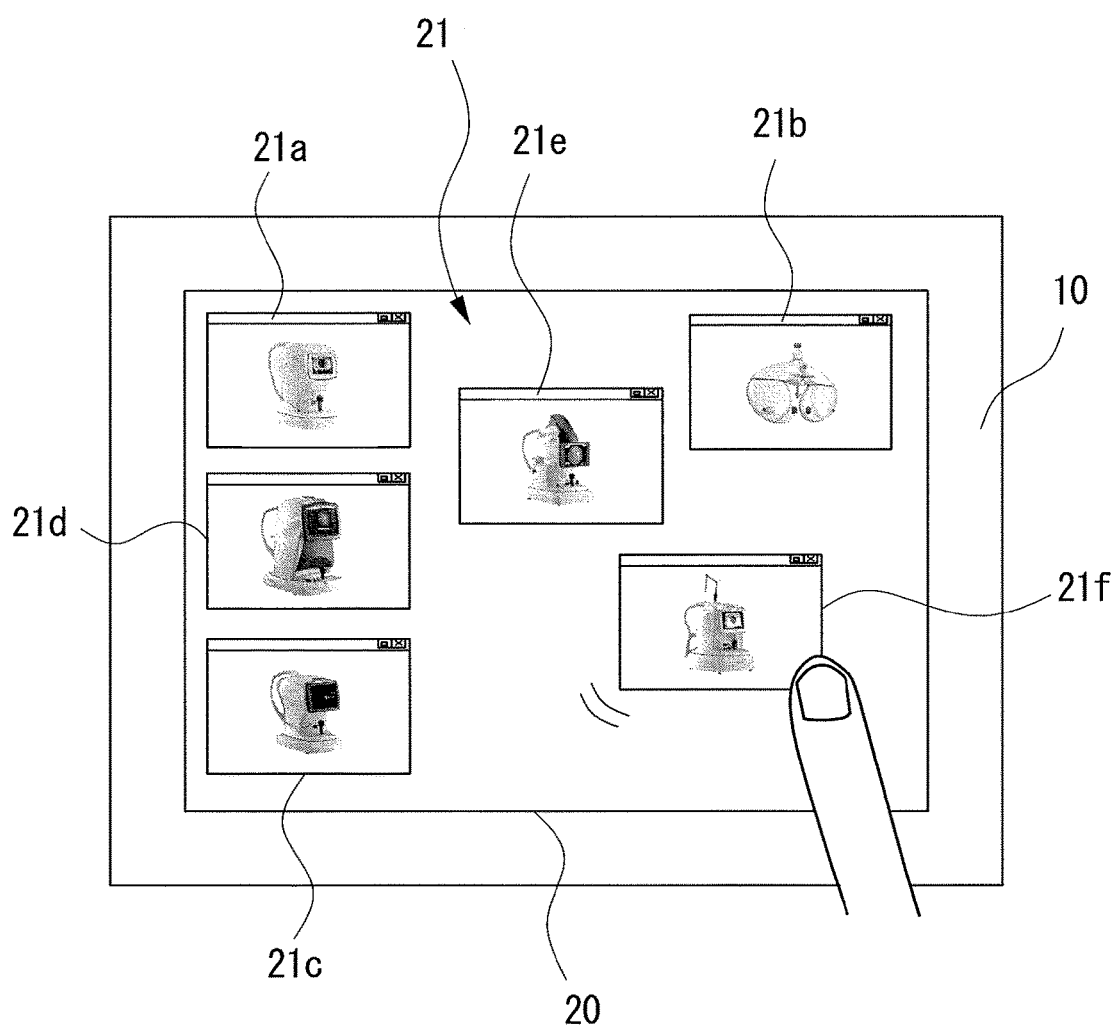
FIG. 10 is a diagram to explain how to change a layout of icons on the terminal device in the example.

The control unit 70 may change the arrangement of the icons 21 displayed on the display unit 75. For instance, as shown in FIG. 10, the control unit 70 may move the display position of each icon 21 on the icon screen 20 based on an operation, such as a drag operation by the examiner. This enables the examiner to change the icon arrangement in conformity to the layout of the ophthalmic apparatuses 1 in an examination room and thus ascertain the correspondence relationship between the apparatuses and the icons.

The control unit 70 may also display the icons 21 against an arbitrary image background. For example, the control unit 70 may superimpose the icons 21 on a layout image having a room wall(s), a partition(s), a desk(s), and others depicted. This enables the examiner to easily ascertain correspondence relationship between the ophthalmic apparatuses 1 displayed on the display unit 75 and the ophthalmic apparatuses 1 placed in the examination room. It is of course that the control unit 70 may superimpose the icons 21 on an image photographed by an unillustrated camera provided in the terminal device 10.

Each of the ophthalmic apparatuses 1 may be provided with a notification unit. This notification unit may be configured to indicate to an examinee or an examiner that measurement and photographing are to be performed from now or that measurement or photographing error or abnormality occurs in the ophthalmic apparatus 1. Examples of the notification unit may include the aforementioned indicator lamp 8, display unit 7a, voice output unit 9a, and others. For instance, the notification unit may turn on or blink the indicator lamp 8, flash or change the color of a screen of the display unit 75, and output a voice from the voice output unit 9a. The notification unit may also display the numbers indicating the measurement order on the display unit 7a to show an examinee or examiner the measurement order, measurement start, or the like.

Each ophthalmic apparatus 1 may be configured to detect the presence of the examinee's face or eye E so that the screens of the relevant ophthalmic apparatus 1 and the terminal device 10 are turned to the active state to enable measurement and operation. For instance, each ophthalmic apparatus 1 may detect the presence of the examinee's face or eye based on a received signal from a light receiving element provided in the optometry unit. Furthermore, for instance, each ophthalmic apparatus 1 may detect the presence of the examinee's face or eye by use of a sensor provided in the face support unit 4.

After the termination of examination using each ophthalmic apparatus 1, all obtained data may be displayed in list form or necessary examination results and analysis results may be calculated from all data and displayed. Further, the data obtained by one ophthalmic apparatus 1 may be transmitted to another ophthalmic apparatus 1 so that the data is utilized in the latter ophthalmic apparatus 1. For instance, the control unit 70 may transmit an AR value measured by an eye refractive power measuring apparatus to a reflector or transmit an ocular axial length measured by an axial length measuring apparatus to an optical tomographic image photographing apparatus, and others. Utilizing measurement data obtained by another apparatus enables fast and reliable measurement.

In a case where measurement data obtained by the ophthalmic apparatus(s) 1 need to be analyzed in detail, the terminal device 10 may transmit the measurement data to a different PC. The terminal device 10 may also obtain an analysis result of the PC and display this analysis result on the display unit 75. Needless to say, the ophthalmic apparatus(s) 1 may directly transmit the measurement data to the PC. In this case, the terminal device 10 may obtain the measurement data and the analysis result via the PC.

The terminal device 10 may transmit data and others of each ophthalmic apparatus 1 to an electronic chart, a filing system, and others and also interface with the electronic chart and others.

The terminal device 10 may further include a photographing unit 80. The control unit 70 may transmit an image (e.g., the face or body of an examiner, etc.) photographed by the photographing unit 80 to the ophthalmic apparatus(s) 1. The control unit 7 may display the image photographed by the photographing unit 80 on the display unit 7a disposed to face the examinee. Thus, the examiner can explain with gestures to the examinee.

The ophthalmic apparatus(s) 1 may transmit an image (e.g., the face of an examinee) photographed by the observation optical system 2a and others to the terminal device 10. The control unit 70 may display the image photographed by the observation optical system 2a on the display unit 75. Thus, the examiner can monitor the examinee.

It may be arranged such that, while the examinee sits in a chair or stool in front of the apparatus, the display unit 7a facing the examinee displays the image of the examiner (the examiner's face and others) from the photographing unit 80, and the display unit 75 facing the examiner displays the image (the examinee's face and others) photographed by the observation optical system 2a. Accordingly, the examiner and the examinee can communicate by voice with each other while seeing each other's images. For instance, the examiner can explain an examination to the examinee and the examinee can ask the examiner some questions and others.

The apparatus may automatically detect that the examinee has sat in front of the apparatus, and thereby may be turned to the active state. For example, a result of received light and others by an optical sensor or the optometry unit 2 may be utilized.

The foregoing embodiments are mere examples and give no limitation to the present disclosure. The scope of the invention is shown by the claims, not in the aforementioned explanation, and may be embodied in other specific forms without departing from the claims and the equivalent signification and range thereto.

What is claimed is:

1. A terminal device to operate a plurality of ophthalmic apparatuses, the terminal device is separate from the plurality of ophthalmic apparatuses, each of the plurality of ophthalmic apparatuses are provided with a respective base table, the terminal device comprising:
    a communication unit comprising a transceiver configured to perform communication with respective transceivers of the plurality of ophthalmic apparatuses;
    a selection receiving unit configured to receive a selection command to select at least one ophthalmic apparatus of the plurality of ophthalmic apparatuses as an operation target to be operated from among the plurality of ophthalmic apparatuses; and
    a controller configured to transmit a control signal to the ophthalmic apparatus selected as the operation target through the communication unit.

2. The terminal device according to claim 1, wherein
    the selection receiving unit includes:
        a display unit configured to display an operational region to operate the ophthalmic apparatus; and
        an operation receiving unit configured to receive an operation from an examiner,
    the controller is configured to:
        cause the display unit to separately display a first operational region to operate a first ophthalmic apparatus and a second operational region to operate a second ophthalmic apparatus different from the first ophthalmic apparatus;
        transmit a first control signal for operating the first ophthalmic apparatus to the first ophthalmic apparatus based on the operation received on the first operational region by the operation receiving unit; and
        transmit a second control signal for operating the second ophthalmic apparatus to the second ophthalmic apparatus based on the operation received on the second operational region by the operation receiving unit.

3. The terminal device according to claim 2, wherein the controller is configured to obtain a first observed image photographed by the first ophthalmic apparatus and a second observed image photographed by the second ophthalmic apparatus from the first and second ophthalmic apparatuses through the communication unit, and to display the first observed image on the first operational region and display the second observed image on the second operational region.

4. The terminal device according to claim 2, wherein the controller is configured to cause the display unit to selectively display the first operational region and the second operational region.

5. The terminal device according to claim 2, wherein the controller is configured to cause the display unit to simultaneously display the first operational region and the second operational region.

6. The terminal device according to claim 2, wherein the controller is configured to set one of the first ophthalmic apparatus and the second ophthalmic apparatus as the operation target based on the operation received on the one of the first operational region and the second operational region by the operation receiving unit.

7. The terminal device according to claim 2, wherein the controller is configured to change the operation target based on the operation received on the one of the first operational region and the second operational region by the operation receiving unit.

8. The terminal device according to claim 2, wherein when the first ophthalmic apparatus is set as the operation target, the controller is configured to cause the display unit to display the first operational region more emphatically than the second operational region for operating the second ophthalmic apparatus which is unset as the operation target.

9. The terminal device according to claim 8, wherein when the first ophthalmic apparatus is set as the operation target, the controller is configured to cause the display unit to display the first operational region in a larger size than the second operational region for operating the second ophthalmic apparatus which is unset as the operation target.

10. The terminal device according to claim 8, wherein the controller is configured to set a measurement order of the plurality of ophthalmic apparatuses based on the operations received by the operation receiving unit and display the operational regions emphatically in turn according to the measurement order.

11. The terminal device according to claim 2, wherein the controller is configured to cause the operational region to display a state of the plurality of ophthalmic apparatuses or a state of an examinee based on a status signal obtained from each of the ophthalmic apparatuses through the communication unit.

12. The terminal device according to claim 2, wherein
the controller is configured to set a measurement order of the plurality of ophthalmic apparatuses based on the operations received by the operation receiving unit and measure the first ophthalmic apparatus and then the second ophthalmic apparatus, and,
after termination of measurement using the first ophthalmic apparatus, the controller switches the first ophthalmic apparatus to an inactive state and the second ophthalmic apparatus to an active state.

13. The terminal device according to claim 2, wherein the controller is configured to cause the first operational region to display a mark symbolizing the first ophthalmic apparatus.

14. The terminal device according to claim 1, wherein the controller is configured to identify whether the plurality of ophthalmic apparatuses are in an active state or an inactive state based on a status signal obtained from each of the ophthalmic apparatuses through the communication unit.

15. The terminal device according to claim 1, wherein the controller is configured to transmit the control signal to the plurality of ophthalmic apparatuses through the communication unit to switch the ophthalmic apparatuses between an active state and an inactive state.

16. The terminal device according to claim 1, further comprising a voice input unit,
wherein the controller is configured to transmit a voice input received from the voice input unit to a voice output unit provided in the ophthalmic apparatus which is the operation target through the communication unit.

17. The terminal device according to claim 1, further comprising a photographing unit, and
wherein the controller is configured to transmit an image received from the photographing unit to an individual display unit provided in the ophthalmic apparatus which is the operation target through the communication unit.

18. A non-transitory storage medium having stored thereon a terminal control program to be used in a terminal device to operate a plurality of ophthalmic apparatuses, the terminal device is separate from the plurality of ophthalmic apparatuses, each of the plurality of ophthalmic apparatuses are provided with a respective base table,
the program being executable by a processor of the terminal device to cause the terminal device to execute the steps of:
receiving a selection command to select at least one ophthalmic apparatus of the plurality of ophthalmic apparatuses which is an operation target to be operated from among the plurality of ophthalmic apparatuses; and
transmitting a control signal to the ophthalmic apparatus selected as the operation target.

19. An optometry system to examine an examinee's eye, comprising:
a plurality of ophthalmic apparatuses to examine the examinee's eye, each of the plurality of ophthalmic apparatuses are provided with a base table; and
a terminal device separate from and configured to electronically communicate with each of the plurality of ophthalmic apparatuses to operate the ophthalmic apparatuses, the terminal device including:
a communication unit comprising a transceiver configured to perform communication with respective transceivers of the plurality of ophthalmic apparatuses;
a selection receiving unit configured to receive a selection command to select at least one ophthalmic apparatus of the plurality of ophthalmic apparatuses as an operation target to be operated from among the ophthalmic apparatuses; and
a controller configured to transmit a control signal to the ophthalmic apparatus selected as the operation target through the communication unit.

* * * * *